US008148131B2

(12) United States Patent
Kang et al.

(10) Patent No.: US 8,148,131 B2
(45) Date of Patent: Apr. 3, 2012

(54) BACTERIOPHAGE AND ANTIBACTERIAL COMPOSITION COMPRISING THE SAME

(75) Inventors: In Hye Kang, Gyeonggi-do (KR); Min Tae Park, Incheon (KR); Young Wook Cho, Seoul (KR); Hyang Choi, Gyeonggi-do (KR); Soo An Shin, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 279 days.

(21) Appl. No.: 12/550,304

(22) Filed: Aug. 28, 2009

(65) Prior Publication Data

US 2010/0135962 A1 Jun. 3, 2010

(30) Foreign Application Priority Data

Dec. 2, 2008 (KR) ........................ 10-2008-0121500

(51) Int. Cl.
*C12N 7/00* (2006.01)

(52) U.S. Cl. .................................................... 435/235.1

(58) Field of Classification Search ........................ None
See application file for complete search history.

(56) References Cited

U.S. PATENT DOCUMENTS

| | | | | |
|---|---|---|---|---|
| 6,485,902 | B2 | 11/2002 | Waddell et al. | |
| 6,942,858 | B1 | 9/2005 | Ghanbari et al. | |
| 2004/0208853 | A1* | 10/2004 | Sulakvelidze et al. ....... | 424/93.6 |
| 2005/0175594 | A1 | 8/2005 | Loessner et al. | |

FOREIGN PATENT DOCUMENTS

| | | |
|---|---|---|
| KR | 2002-0043585 | 6/2002 |
| KR | 2002-0075783 | 10/2002 |
| KR | 10-2006-0023183 | 3/2006 |
| WO | WO 2005/024005 A1 | 3/2005 |

OTHER PUBLICATIONS

Al-Tarazi et al., Asian-Aust. J. Anim. Sci., 2003, 16(1):77-82.*

Loessner et al., Journal of General Microbiology, 1993, 139:2627-2633.*

Kwon, H-J., et al., "Characterization of a T7-Like Lytic Bacteriophage (ΦSG-JL2) of *Salmonella enterica* Serovar Gallinarum Biovar Gallinarum," *Appl. Environ. Microbiol. 74*(22): 6970-6979, American Society for Microbiology, United States (2008).

Woods, D., et al., "*Burkholderia thailandensis* E125 Harbors a Temperate Bacteriophage Specific for *Burkholderia mallei,*" *J. Bacteriol.* 184(14): 4003-4017, American Society for Microbiology, United States (2002).

International Search Report for International Application No. PCT/KR2009/004582, Korean Intellectual Property Office, Republic of Korea, mailed Mar. 29, 2010.

English language abstract of Korean Patent Publication No. KR 10-2006-0023183 (listed as document FP3 on accompanying PTO/SB/08a equivalent).

English language abstract of Korean Patent Publication No. KR 2002-0043585 (listed as document FP4 on accompanying PTO/SB/08a equivalent).

English language abstract of Korean Patent Publication No. KR 2002-0075783 (listed as document FP3 on accompanying PTO/SB/08a equivalent).

* cited by examiner

*Primary Examiner* — Zachariah Lucas
*Assistant Examiner* — Nicole Kinsey White
(74) *Attorney, Agent, or Firm* — Sterne, Kessler, Goldstein & Fox P.L.L.C.

(57) ABSTRACT

The present invention relates to a novel bacteriophage, more particularly, a bacteriophage that has a specific bactericidal activity against Fowl Typhoid causing *Salmonella* Gallinarum (SG) and Pullorum disease-causing *Salmonella* Pullorum (SP). Further, the present invention relates to a composition for the prevention or treatment of infectious diseases caused by *Salmonella* Gallinarum or *Salmonella* Pullorum, comprising the bacteriophage as an active ingredient. Furthermore, the present invention relates to feed and drinking water for poultry, sanitizers and cleaners, comprising the bacteriophage as an active ingredient.

8 Claims, 9 Drawing Sheets

SEQUENCE LISTING

<160> NUMBER OF SEQ ID NOS: 19

<210> SEQ ID NO 1
<211> LENGTH: 1355
<212> TYPE: DNA
<213> ORGANISM: Bacteriophage KCCM10969P

<400> SEQUENCE: 1
cggaagcgtc agatctggaa tcacagttca acggctggct gcagggtaac ctgctcgtca 60
tcgtggaaga actgaaaacc gacgacaagc acacactgct ggaacgaatg aagccgatga 120
tcaccaacaa gcgcattcaa atccagcaga aaggtatcga ccagacgacc ggcgataacc 180
gtgcaaactt tatctgtttc tcaaaccacc gcgactgcgt gccgattaaa cgtaacggcc 240

```
gccgctatgc catgctgtac acggcgcaac agagcgttga agacctgcag cgcgacgaca    300

tgccgccgga ttatttctat cgtctgtatg agtgggctga caacggcggc tgggcggtca    360

tcgcacactt cctgtctgaa tacgagatac cggatgaatt caacccgaaa acattctgtc    420

agcgtgcacc ggagacatcc agccagcgcg aagcggaaaa agtatcactg ggacgcgttg    480

aacaggaaat catggaagct gtagacagcg agatgccggg attctgtgac ggatggatca    540

gcagttacca cctgaccaaa ctgctggaaa gcaaagggct ggaacgcttc ctgccaccga    600

acaagcgcaa acagaccctg gaggacatcg gctacgtgca gcaccctaac ctgaataacg    660

gacgtgtgaa caatgcgatc gcgggggaag gtaagccgcg cctgtacgtc gataaaatcc    720

gtaaagacct gctgaatatc aaagcaccgg gggaaattgc cgatatgtac tggaagtcgc    780

agaacccgtt tgcgggaggt gcggtgtgac taaacgtgct gtgtttctgt atgacgtgac    840

gggcatcgct gcccgtccat ggatagatgc cggatatgaa tgctggttat tcgacgggca    900

acatcctaaa ggtattacgc gtgaaggtaa catggtgaaa gtcgggatgt ggtttcacca    960

tgaccagtgt gatgaacatg cggaatggat aaaaagtcag gttataaacg ccgaaatcgt   1020

aatcggattt ccggagtgta ctgatctgac tgtcgccggc gcgcgttggt ggaaagacaa   1080

acgagaagcg gatccggatt ttcagaacaa ggcaaaatgt cttgcactgc tcgttgaaaa   1140

ggtcggtaat gcactggaat gtccatggtg ctttgaaaat ccggtgggag cattatcaaa   1200

tttatacaga ttgccggatt tcacgtttaa cccttgcgac tatgcaggtt atttagactg   1260

tgactcgccg caccccattt atccggaagt ttacccggtt caggatcgct ataataaaaa   1320

cacctgtatc tggtgcggta acggctttgt acagc                              1355
```

```
<210> SEQ ID NO 2
<211> LENGTH: 1930
<212> TYPE: DNA
<213> ORGANISM: Bacteriophage KCCM10969P

<400> SEQUENCE: 2

ggtgtcgtaa caagtgtcgc cggactaacc ctgtatttga gtgaccctgt agaattactg     60

cccggttata cctatagtat tactctaaca ggccgtctgg gtacactgga aaatgtacct    120

atcacttccg gtgtagacga attcagtgtg gtgttacaat cagtaccgga tcaagaggtt    180

tatacagggt ggatgcgtga ccgtacagcc tatgtgattc gcactgacga cgagcgtaca    240

aaactcgcta tgctagttca gagtatggag ccatcagggc gtgacaacaa ctatcaggta    300

gggttaacgt gcatcaatta cgatgcacgt tattatcagg atgataaata accacccatg    360

aaaaaaaaaa ctaaccccgc ttcggcgggg ttttgttatg tattaaaatt aaagtgagta    420

tgttacataa cttccatctg gtttttagc cagcaatctc aatgccccat cacttccgaa    480

gaagaaacct atagatgagt tatgctctaa agcactctct ggtaattgtg aagacgcaac    540

aggtatgctc atatgcttaa agcctaagcg attaagctga aactcaccta cacgtacacc    600

gtcctggatt gctgaaagct taactatact tgcctcacct cctggcgttg ccacttggca    660

atctgctgtc ataagcaatg atgggtttgt tgtgcccccc attgctggac gcatagccag    720

ggtcatggtg ttatcaccat gctgtacgtt tatgtttcca ccctgaatat cgccaacata    780

cgtacacaat aattttttg tcccactccc agcacatgaa acattgctaa tctctgaaga    840

aggcgcatat accgcatatc cttgcgtggt atatgcatgt accattactc ctctcaaacg    900

actcccaccc tcacaaacaa tctggtttaa gttagtaagg tctttatttg ccccaatcac    960

tgttatcttg gtgatatcat tgtttgtacc tctgtcgaaa atcccctctt tatgggcctc   1020
```

```
ataggttaca atattatcaa tgatattttt ttgcccatcc caccacgcac caatccccat   1080

gcaatcacgc gtaatgatat tgcgtatgat gtgctgagta ggtaaatgga accacgggta   1140

ttcagccaga gtgtaatcgt ctatacgttc ggttggcgac cctgtgtcag cattaacatc   1200

aatcccatcg taataacatt gaatcgtagt tatattatca aacaccagtc ggtagtttct   1260

tgcggaacgt ccgcctatct cattctggta agtcttaaca cctgattcgc cgacacgata   1320

cgagataagg tcgcgcacgc caccatcgtg atcgtcacca ccgtcatttc tgataaataa   1380

aactgcagag ccagaaccat atttaatctc cccgccaacg accttattgc cggtccccca   1440

ctcagttgtg tgatggttct cgaacgtaat tccagactcc caggcaataa aattacgtgg   1500

agattcaact aaaatgtgat tgcagagagt gaaaagatac cctcccatag tagcttctgg   1560

atgagtaacc ttgatattat tagcggagtt tacacgtaag gtggcaccag caacctggtt   1620

tttaatggaa tcaggaaggg acgcccaaat gtcatggtca ttaacattag gtttataccc   1680

cttgtctaga cgctgagtaa ccgacgctaa taccgtggtc gggtttgtca cccagttccc   1740

attatcatca aaacggtata cagtataagg agttgttttg gtgtgaatgt gcggtgaaat   1800

aattctggaa ccactaccta agttattaaa gttgaggact ccatcaccaa taaacttagc   1860

tttacagtcg attgttaaca cctttccgcc aaaatcaact gtctcgttgt cggtgaatgt   1920

atagtcgcgg                                                          1930
```

```
<210> SEQ ID NO 3
<211> LENGTH: 958
<212> TYPE: DNA
<213> ORGANISM: Bacteriophage KCCM10969P

<400> SEQUENCE: 3

tttcgaactt ctgaacgccg cgagtcagtg cgtatttagt cacccagata gtctcagcat     60

gaagtgatgc gctgaccagg agggtgagga gtgatacaca gcacttagta atcatgagac    120

gggcctaaag atggtaaata agtgaaactg gcacatacat tcaacgcatc accgggtact    180

accacctctt gcccattatt agttacatca agccagaaac atctataatt ttctcctaac    240

ttttcaacaa tcgtcattgg gcactgcggg ttagatggta aacaaacggt ctgccctata    300

ttaaactctt tcatctcgta cactccgcga ttaattattt tatactttag accaaagaaa    360

accgcacgtc aatgcggtaa ttcgtcgccg ttatcacatt tcacaatgtt aacccggcgg    420

cttgctgtcg tcacagccat taagataaga tcaccccctg tcggttgtga ctaactgaat    480

actagcccac cttacccaga ccgtcaatct ttcctgcaac gattgcggcg taaattgcgg    540

tggccgagtt aagcgggtcg acaccgtgac agtcgataat ggtcagcatc tgatcgatcg    600

ctttgttgcg ttctgtacga agcggacgga attcttgcaa cttgtctaaa atcaggtcac    660

gagaaatatc caccccaaaa cctacatttt cttcaatact cctcatcaca atgacccaca    720

ttgacagata cattactctt actttagtcc aaccctcttt cgacgatgaa tcgaaccatt    780

cacactcagt accaactggc ggcagaccgg taccgtccca cttttcgccg cgcagcagtt    840

tttcaagcct ttttcgacca tcaagttgat gtcaacaaag tatcggctac cgcggtagtc    900

aaatcgaaca ccgaaaggtt cgttcagaca ccatgtttta acgccaagtt tggtgata      958
```

```
<210> SEQ ID NO 4
<211> LENGTH: 999
<212> TYPE: DNA
<213> ORGANISM: Bacteriophage KCCM10969P

<400> SEQUENCE: 4
```

```
cacgaacgtc tgcgcgtcgg taagaaaacc atgatgggcg gagcgtacaa actggcgctg     60

aacggtacgt acggcaacag taacaacgag tacagcccgt tttatgaccc gatgtacacg    120

atgaaaatca ccatcaatgg tcagttgtcg ctgtgtatgc tcgtcgaaca gttaatcaaa    180

gtgcccgggc tgcgtatggt ccagtgcaac accgacggta tcactttcca ctgccccgtt    240

gaatatgtcg accatgctca caacctgcgc ctgtggtggg aacaactgac gaaactcgaa    300

ctggaagaga caaggtacag tagatttttc atcagagatt gtaataacta catcgcagaa    360

cttgaataac tacattgctt gcgatagagt gttagcaaaa gggagaaacg ttatgacacc    420

tatcgcaggc ttgaaaaaca aaccttgtat ctattccatc ttgaacaaag tcaacggtaa    480

gatttatgta gggaaaacta aatgcttata tcgtcgttgc taccagtatt tgggcgcatt    540

taaaaacaaa agtcagggaa agataaatca atatctgttg aactctttcg aaaaatatgg    600

aattgataat tttgaaatgt taccgatcga gttttgtgat atttcaaaaa tcgatgagcg    660

agaactttac tggatatccg aacttagaac tacggaaaaa aataaaggtt acaatcttcg    720

attagactca tctaccggta tgattaccca ccgaagaacc tcggagaaaa taagtaataa    780

cctgaaaaaa caatgggctg ccggtgtaag agattcgcat tcagacaaac tgaaagaatc    840

ttggaaaaat aatcctcaac gtaaaactat ccaaagtgaa ttgttcacga agtataaaac    900

taaatattgt tatgttattc atttgcctga ctcatcatgt ttagttttga attataaagg    960

gttgaaatca atgaaactac atacctctgt acttagttg                           999
```

```
<210> SEQ ID NO 5
<211> LENGTH: 999
<212> TYPE: DNA
<213> ORGANISM: Bacteriophage KCCM10969P

<400> SEQUENCE: 5

cgatgcatgt cgcatttaat tgtgttacag cgtattcaat cgcccgtccg ccggatgaaa     60

acgatccgcg tacggaagaa acgaaatggt caacgcccgg gatagtgaac gggctgcacg    120

tgacacgctg acctgatggc gggttgttat gcatccacca gtcataatca gcggccagta    180

cgacgtcagg ctgtgatatg agatagcagg cgttgtttac agcgatttta aagcagtcct    240

gtgcgttcac ccactcaatc tgtgcctgtg tgagcgacgg acccgtagcg acgcacagaa    300

cgcgcattaa cgcaccacct cggcggtgaa cggtacaaca acggtctgca ggtaccattc    360

gtcatcacga ccttctgtct cgatgcgcac gcccgttggt tgaccgtaat tgatgcacgg    420

atccgcccat tgcccctcga atgcctgtac aagctgttcg cacagttcgt cgttcgggaa    480

tacaccctgc tgcattggcg taaagacgtt cacataagcg ataccgatac ggtcacggcg    540

gcgcgatacg ccttcaccgc ccagggtggt aattccaccg gcgttaaact gcacggtgag    600

tcgaacccag gtatcagttg ttttcggatc gtatttctcg ccgtcaattt ccaccccgtc    660

aacaatcaga ccgagattca gcaaacgggt ggtgatcacg gcgcggatat cattaatcgt    720

cacgattgat agccctgtaa ttagtagaat gtgtgaaacg cgtaatttca atctgcacag    780

cacgatccac aaaaccagcg ggtgattgtt gtgaccagcc gttattcagt cggttaatgt    840

aaggcgtatt gttggtgata taaatgacgc ctttcgatgg ttcataagtt aatatgtcag    900

ccagcccgga cgactgcttt gactgtgctg acgcaacatc accttttgac ccgtcattgc    960

ctgttggtgc tgtaccagct gatacccacc agtttgcag                           999

<210> SEQ ID NO 6
<211> LENGTH: 20
```

<212> TYPE: DNA
<213> ORGANISM: Artificial Sequence
<220> FEATURE:
<223> OTHER INFORMATION: Primer

<400> SEQUENCE: 6
cgtcagatct ggaatcacag 20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cgtccgttat tcaggttagg 20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ggtgtcgtaa caagtgtcgc 20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
gcttatgaca gcagattgcc 20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
cctgctcgtc atcgtggaag 20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gccgttaccg caccagatac 20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ccctgtagaa ttactgcccg 20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ccgcgactat acattcaccg 20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ctttcgaact tctgaacgcc 20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tatcaccaaa cttggcgtta 20

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
cacgaacgtc tgcgcgtcg 19

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
caactaagta cagaggtat 19

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tcgatgcatg tcgcatttaa 20

<210> SEQ ID NO 19
<211> LENGTH: 20
<212> TYPE: DNA
<213> ORGANISM: Artificial Sequence -continued

```
<220> FEATURE:
<223> OTHER INFORMATION: Primer

<400> SEQUENCE: 19

ctgcaaactg gtgggtatca                                                   20
```

BACTERIOPHAGE AND ANTIBACTERIAL COMPOSITION COMPRISING THE SAME

CROSS REFERENCE TO RELATED APPLICATIONS

This application claims the benefit of Korean Patent Application No. 10-2008-0121500, filed Dec. 2, 2008, which is incorporated by reference in its entirety.

REFERENCE TO SEQUENCE LISTING SUBMITTED ELECTRONICALLY VIA EFS-WEB

The content of the electronically submitted sequence listing (Name: 2511.0040000 Sequence Listing.TXT; Size: 11,986 bytes; and the Date of Creation: Aug. 28, 2009) filed herewith the application is incorporated by reference in its entirety.

BACKGROUND OF THE INVENTION

1. Field of the Invention

The present invention relates to a novel bacteriophage, more particularly, a bacteriophage that has a specific bactericidal activity against Fowl Typhoid causing *Salmonella* Gallinarum (SG) and Pullorum disease-causing *Salmonella* Pullorum (SP). Further, the present invention relates to a composition for the prevention or treatment of infectious diseases caused by *Salmonella* Gallinarum or *Salmonella* Pullorum, comprising the bacteriophage as an active ingredient. Furthermore, the present invention relates to feed and drinking water for poultry, sanitizers and cleaners, comprising the bacteriophage as an active ingredient.

2. Background Art

*Salmonella* is a genus of the family Enterobacteriaceae, characterized as Gram-negative, facultatively anaerobic, non spore-forming, rod-shaped bacteria, and most strains are motile by flagella. *Salmonella* has an average genome GC content of 50-52%, which is similar to those of *Escherichia coli* and *Shigella*. The genus *Salmonella* is a pathogenic microorganism that causes infections in livestock as well as in humans. *Salmonella enterica*, a species of *Salmonella* bacterium, has a variety of serovars including *Salmonella* Gallinarum, *Salmonella* Pullorum, *Salmonella* Typhimurium, *Salmonella* Enteritis, *Salmonella* Typhi, *Salmonella* Choleraesuis and *Salmonella* derby (Bopp C A, Brenner F W, Wells J G, Strokebine N A. *Escherichia, Shigella, Salmonella*. In Murry P R, Baron E J, et al eds Manual of clinical Microbiology. 7th ed. Washington D.C. American Society for Microbiology 1999; 467-74; Ryan K J. Ray C G (editors) (2004)). Of them, *Salmonella* Typhimurium and *Salmonella* Enteritis are pathogenic for human and animals, *Salmonella* Typhi is a human-adapted pathogen, *Salmonella* Choleraesuis and *Salmonella* derby are swine-adapted pathogens, and *Salmonella* Gallinarum and Pullorum are fowl-adapted pathogens. Each serovar causes illness in that species, which results in tremendous damage to farmers and/or consumers.

A disease of domestic birds caused by *Salmonella* bacterium is Fowl Typhoid (FT), which is caused by a pathogen, *Salmonella* Gallinarum (hereinbelow, designated as SG). Fowl Typhoid (FT) is a septicemic disease of domestic birds such as chicken and turkey, and the course may be acute or chronic with high mortality. Recently, it has been reported that Fowl Typhoid frequently occurs in Europe, South America, Africa, and South-East Asia, and damages are increasing. Outbreaks of FT in Korea have been reported since 1992 and economic losses coupled by FT in brown, egg-laying chickens are very serious (Kwon Yong-Kook. 2001 annual report on avian diseases. information publication by National Veterinary Research & Quarantine Service. March, 2001; Kim Ae-Ran et al., The prevalence of pullorum disease-fowl typhoid in grandparent stock and parent stock in Korea, 2003, Korean J Vet Res (2006) 46(4): 347353). Pullorum Disease is also caused by one of the *Salmonella* bacteria, *Salmonella* Pullorum (hereinbelow, designated as SP). Pullorum disease occurs in any age or season, but young chicken is very susceptible to the disease. During the past one century, it has been a serious disease to young chickens at 1-2 weeks of age or younger by egg-transmitted infections in the world and Korea. Since the 80's, the occurrence has greatly decreased. However, it has been growing in the middle of the 90's.

In Korea, the outbreaks of Fowl Typhoid and Pullorum disease have been increasing since the 90's, inflicting economic damages to farmers. For this reason, a live attenuated SG vaccine has been used in broilers for the prevention of Fowl Typhoid from 2004 (Kim Ae-Ran et al., The prevalence of pullorum disease-fowl typhoid in grandparent stock and parent stock in Korea, 2003, Korean J Vet Res (2006) 46(4): 347~353), while its efficacy is doubtful, and the live vaccine is not allowed to be used for layers because of the risk of egg-transmitted infections. Unfortunately, there are still no commercially available preventive strategies against Pullorum disease, unlike Fowl Typhoid. Thus, there is an urgent need for new ways to prevent Fowl Typhoid and Pullorum disease.

A Bacteriophage is a specialized type of virus that only infects and destroys bacteria, and can self-replicate only inside a host bacteria. A Bacteriophage consists of genetic material—the nucleic acid—single or double stranded DNA or RNA surrounded by a protein shell. There are three basic structural forms of bacteriophage: an icosahedral (twenty-sided) head with a tail, an icosahedral head without a tail, and a filamentous form. Bacteriophages are classified based on their morphological structure and genetic material. Based on their tail structure, bacteriophages having icosahedral head and double-stranded, linear DNA as their genetic material are divided into three families: Myoviridae, Siphoviridae, and Podoviridae, which are characterized by contractile, long noncontractile, and short noncontractile tails, respectively. Bacteriophages having icosahedral head without a tail and RNA or DNA as their genetic material are divided based on their head shape and components, and the presence of shell. Filamentous bacteriophages having DNA as their genetic material are divided based on their size, shape, shell, and filament components (H. W. Ackermann, Frequency of morphological phage descriptions in the year 2000; Arch Virol (2001) 146:843-857; Elizabeth Kutter et al. Bacteriophages biology and application; CRC press). During infection, a bacteriophage attaches to a bacterium and inserts its genetic material into the cell. After this a bacteriophage follows one of two life cycles, lytic or lysogenic. Lytic bacteriophages take over the machinery of the cell to make phage components. They then destroy or lyse the cell, releasing new phage particles. Lysogenic bacteriophages incorporate their nucleic acid into the chromosome of the host cell and replicate with it as a unit without destroying the cell. Under certain conditions, lysogenic phages can be induced to follow a lytic cycle (Elizabeth Kutter et al. Bacteriophages biology and application, CRC press).

After the discovery of bacteriophages, a great deal of faith was initially placed in their use for infectious-disease therapy. However, when broad spectrum antibiotics came into common use, bacteriophages were seen as unnecessary because of having a specific target spectrum. Nevertheless, the misuse and overuse of antibiotics resulted in rising concerns about antibiotic resistance and harmful effects of residual antibiotics in foods (Cislo, M et al. Bacteriophage treatment of suppurative skin infections. Arch Immunol. Ther. Exp. 1987.2: 175-183; Kim sung-hun et al., Bacteriophage; New Alternative Antibiotics. biological research information center. BRIC). In particular, antimicrobial growth promoter (AGP), added to animal feed to enhance growth, is known to induce antibiotic resistance, and therefore, the ban of using antimicrobial growth promoter (AGP) has been recently introduced. In the European Union, the use of all antimicrobial growth promoters (AGPs) was banned from 2006. Korea banned the use of some AGPs, and is considering restrictions on the use of all AGPs.

These growing concerns about the use of antibiotics have led to a resurgence of interest in bacteriophage as an alternative to antibiotics. 7 bacteriophages for control of *E. coli* O157:H are disclosed in U.S. Pat. No. 6,485,902 (applied for in 2002—Use of bacteriophages for control of *Escherichia coli* O157). 2 bacteriophages for control of various microorganisms are disclosed in U.S. Pat. No. 6,942,858 (applied for by Nymox in 2005—Compositions containing bacteriophages and method of using bacteriophages to treat infections). Many companies have been actively trying to develop various products using bacteriophages. EBI food system (Europe) developed a food additive for preventing food poisoning caused by *Listeria monocytogenes*, named Listex-P100, which is the first bacteriophage product approved by the US FDA. A phage-based product, LMP-102 was also developed as a food additive against *Listeria monocytogenes*, approved as GRAS (Generally regarded as safe). In 2007, a phage-based wash produced by OmniLytics was developed to prevent *E. coli* 0157 contamination of beef during slaughter, approved by USDA's Food Safety and Inspection Service (FSIS). In Europe, *Clostridium sporogenes* phage NCIMB 30008 and *Clostridium tyrobutiricum* phage NCIMB 30008 were registered as a feed preservative against *Clostridium* contamination of feed in 2003 and 2005, respectively. Such studies show that research into bacteriophages for use as antibiotics against zoonotic pathogens in livestock products is presently ongoing.

BRIEF SUMMARY OF THE INVENTION

Technical Problem

In order to solve the problems generated by the use of broad spectrum antibiotics, the present inventors isolated a novel *Salmonella* bacteriophage from natural sources, and identified its morphological, biochemical, and genetic properties. The present inventors found that the bacteriophage has a specific bactericidal activity against *Salmonella* Gallinarum (SG) and *Salmonella* Pullorum (SP) without affecting beneficial bacteria, and excellent acid-, heat- and dry-resistance, and thus can be applied to various products for the control of *Salmonella* Gallinarum (SG) and *Salmonella* Pullorum (SP), including feed and drinking water for poultry, sanitizers, and cleaners, in addition to a composition for the prevention and treatment of infectious diseases caused by *Salmonella* Gallinarum and *Salmonella* Pullorum, in particular, Fowl Typhoid and Pullorum Disease, thereby completing the present invention.

Technical Solution

It is an object of the present invention to provide a novel bacteriophage having a specific bactericidal activity against *Salmonella* Gallinarum and *Salmonella* Pullorum.

It is another object of the present invention to provide a composition for the prevention and treatment of infectious diseases caused by *Salmonella* Gallinarum and *Salmonella* Pullorum, comprising the bacteriophage as an active ingredient.

It is still another object of the present invention to provide a feed and drinking water for poultry, comprising the bacteriophage as an active ingredient.

It is still another object of the present invention to provide a sanitizer and cleaner, comprising the bacteriophage as an active ingredient.

It is still another object of the present invention to provide a method for preventing and treating infectious diseases, Fowl Typhoid or Pullorum disease caused by *Salmonella* Gallinarum or *Salmonella* Pullorum using the composition comprising the bacteriophage as an active ingredient.

Advantageous Effects

The novel bacteriophage of the present invention has a specific bactericidal activity against *Salmonella* Gallinarum and *Salmonella* Pullorum, and excellent acid-, heat- and dry-resistance, and thus can be used for the prevention and treatment of infectious diseases caused by *Salmonella* Gallinarum or *Salmonella* Pullorum, including Fowl Typhoid and Pullorum disease, and also used for the control of *Salmonella* Gallinarum and *Salmonella* Pullorum.

BRIEF DESCRIPTION OF THE DRAWINGS/FIGURES

FIG. 1 is an electron microscopy photograph of ΦCJ1, in which ΦCJ1 belongs to the morphotype group of the family Siphoviridae, characterized by isometric capsid and long non-contractile tail;

FIG. 2 is the result of SDS-PAGE of the isolated bacteriophage ΦCJ1, in which protein patterns of the bacteriophage are shown, major proteins of 38 kDa and 49 kDa and other proteins of 8 kDa, 17 kDa, 80 kDa, and 100 kDa (See-blue plus 2 prestained-standard (Invitrogen) used as a marker);

FIG. 3 is the result of PFGE of the isolated bacteriophage ΦCJ1, showing the total genome size of approximately 61 kbp (5 kbp DNA size standard (Bio-rad) as a size marker);

FIG. 4 is the result of PCR, performed by using each primer set of ΦCJ1 genomic DNA, in which (A; PCR amplification using primer set of SEQ ID NOs. 6 and 7, B; PCR amplification using primer set of SEQ ID NOs. 10 and 11, C; PCR amplification using primer set of SEQ ID NOs. 8 and 9, D; PCR amplification using primer set of SEQ ID NOs. 12 and 13) each of A, B, C and D lanes had a PCR product of approximately 660 bp, 1.3 kbp, 670 bp, and 1.8 kbp;

Figure 8:
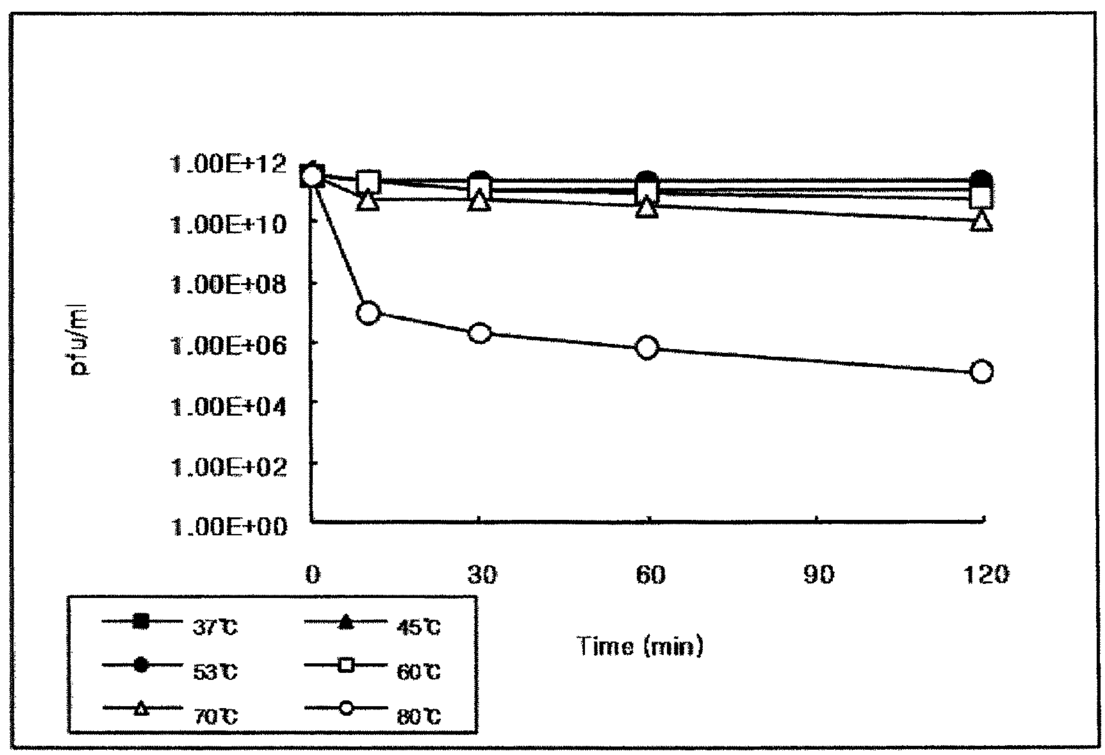
Figure 9:
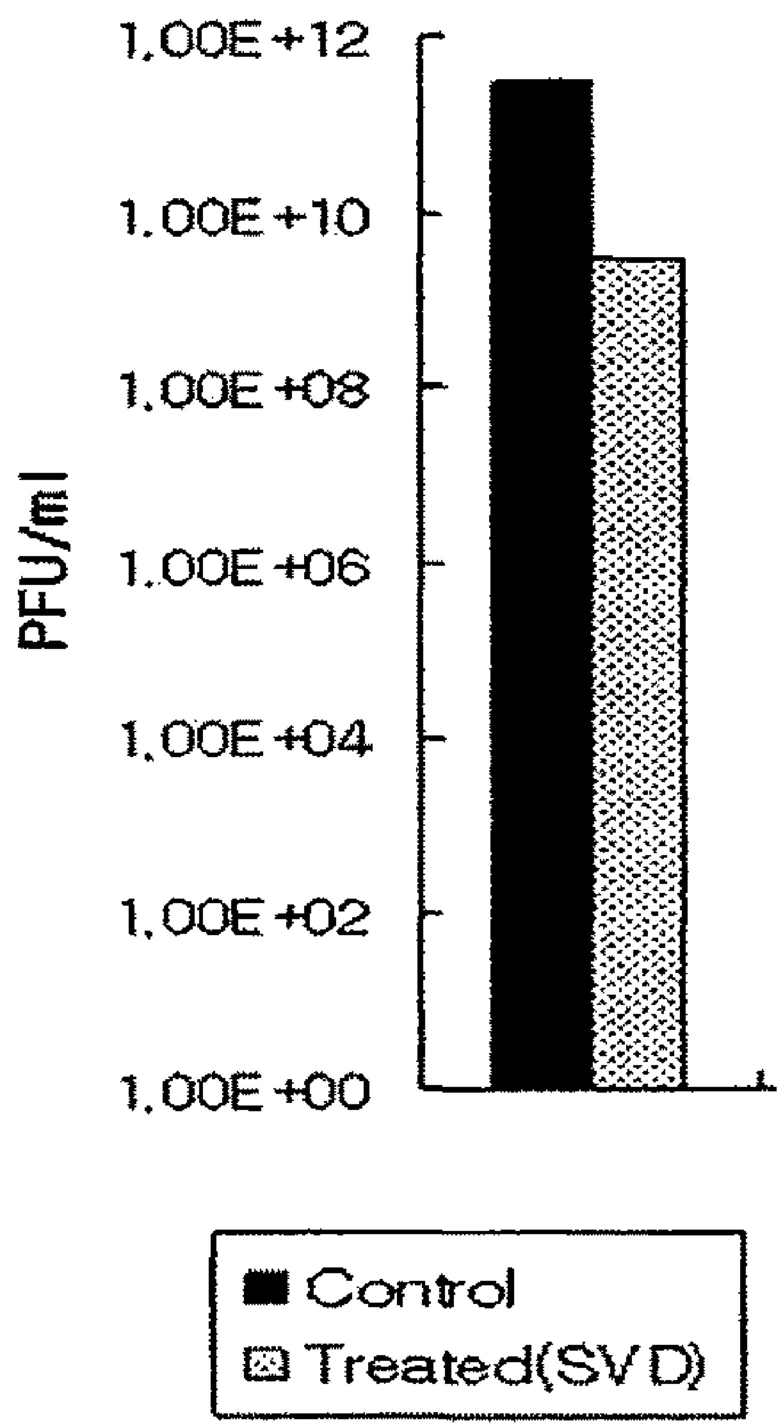

FIG. 8 is the result of a heat-resistance test on the bacteriophage ΦCJ1, showing the number of surviving bacteriophage at 37, 45, 53, 60, 70, 80° C., and a time point of 0, 10, 30, 60, 120 min, in which the bacteriophage ΦCJ1 did not lose its activity even after exposure at 70° C. for 2 hrs, and its activity was decreased after exposure at 80° C. for 10 min, but maintained constantly; and FIG. 9 is the result of a dry-resistance test on the bacteriophage ΦCJ1, performed at 60° C. for 120 min using a speed vacuum dryer (SVD), in which changes in the titers before and after drying were compared to examine the relative stability, and its activity was decreased to $10^2$.

BEST MODE

In accordance with an aspect, the present invention relates to a novel bacteriophage having a specific bactericidal activity against *Salmonella* Gallinarum and *Salmonella* Pullorum.

The bacteriophage of the present invention belongs to the morphotype group of the family Siphoviridae, characterized by isometric capsid and long non-contractile tail, and has a total genome size of 61 kbp and major structural proteins with a size of 38 kDa and 49 kDa.

The bacteriophage of the present invention has the capability of selectively infecting *Salmonella* Gallinarum and *Salmonella* Pullorum, namely, species specificity.

Further, the bacteriophage of the present invention has a total genome size of approximately 61 kbp, and may include a nucleic acid molecule represented by SEQ ID NOs. 1 to 5 within the entire genome.

As used herein, the term "nucleic acid molecule" encompasses DNA (gDNA and cDNA) and RNA molecules, and the term nucleotide, as the basic structural unit of nucleic acids, encompasses natural nucleotides and sugar or base-modified analogues thereof.

Further, the bacteriophage of the present invention has the biochemical properties of acid- and heat-resistance, in which it can stably survive in a wide range of pH environment from pH 2.5 to pH 9.0, and in a high temperature environment from 37° C. to 70° C. In addition, the bacteriophage of the present invention has dry-resistance to stably maintain even after high-temperature drying (at 60° C. for 120 minutes). Such properties of acid-, heat-, and drying-resistance also allow application of the bacteriophage of the present invention under various temperature and pH conditions, upon the production of prophylactic or therapeutic compositions for poultry diseases caused by SG and SP, and other products comprising the bacteriophage as an active ingredient.

The present inventors collected sewage samples at chicken slaughterhouse, and isolated the bacteriophage of the present invention that has a SG and SP-specific bactericidal activity and the above characteristics, which was designated as ΦCJ1 and deposited at the Korean Culture Center of Microorganisms, located at 361-221, Yurim B/D, Hongje-1-dong, Seodaemun-gu, Seoul, 120-091, Republic of Korea, on Oct. 24, 2008 under accession number KCCM10969P.

Figure 1:
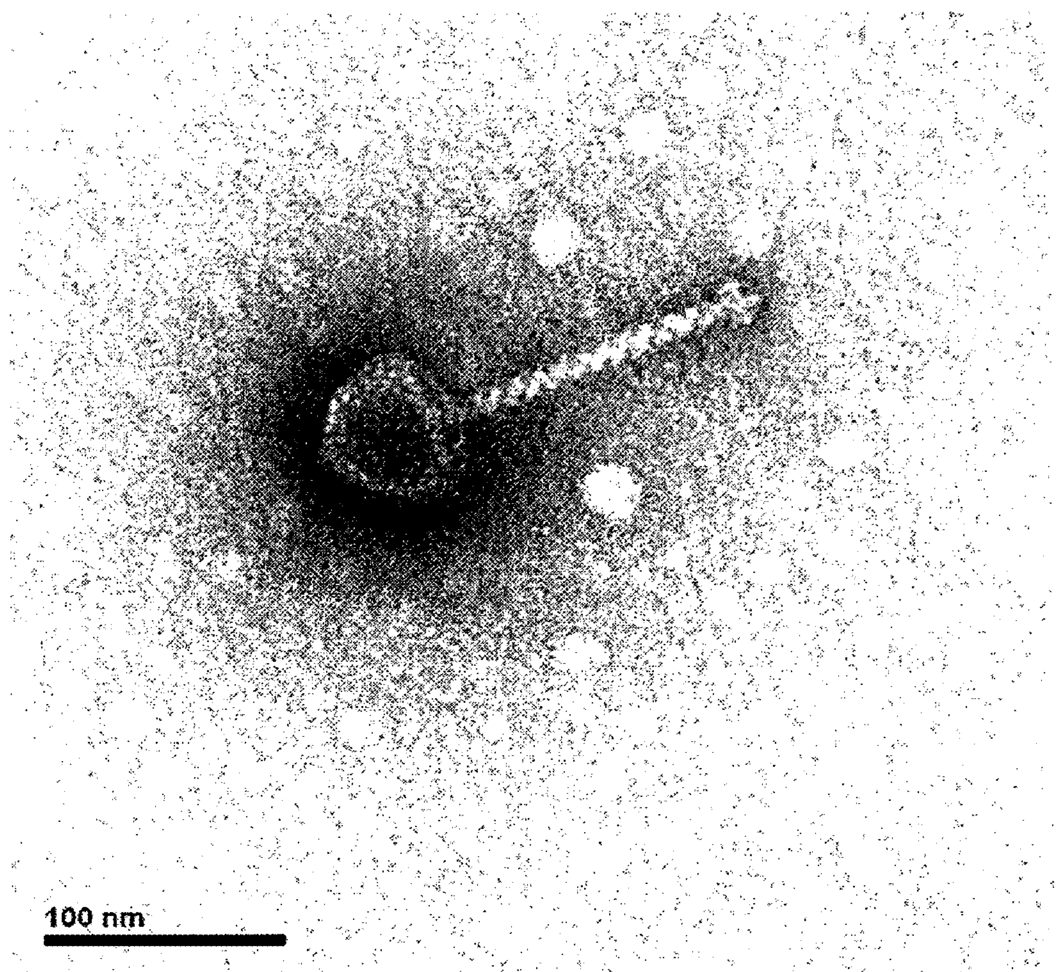

In accordance with the specific Example of the present invention, the present inventors collected sewage samples at a chicken slaughterhouse to isolate bacteriophages that lyse the host cell SP, and they confirmed that the bacteriophages are able to lyse SG and SP, specifically. Further, they examined the bacteriophage (ΦCJ1) under electron microscope, and found that it belongs to the morphotype group of the family Siphoviridae (FIG. 1).

The protein patterns of the bacteriophage ΦCJ1 were also analyzed, resulting in that it has major structural proteins with a size of 38 kDa and 49 kDa.

The total genome size of the bacteriophage ΦCJ1 was also analyzed, resulting in that it has a total genome size of approximately 61 kbp. The results of analyzing its genetic features showed that the bacteriophage includes a nucleic acid molecule represented by SEQ ID NOs. 1 to 5 within the total genome. Based on these results, genetic similarity with other species was compared. It was found that the bacteriophage showed very low genetic similarity with the known bacteriophages, indicating that the bacteriophage is a novel bacteriophage. More particularly, the ΦCJ1-specific primer set, e.g., SEQ ID NOs. 6 and 7, 10 and 11, 8 and 9, 12 and 13, 14 and 15, 16 and 17, and 18 and 19, were used to perform PCR. Each PCR product was found to have a size of 660 bp, 1.3 kbp, 670 by 1.8 kbp, 1 kbp, 1 kbp and 1 kbp.

Further, when SG and SP were infected with ΦCJ1, the phage plaques (clear zone on soft agar created by host cell lysis of one bacteriophage) showed the same size and turbidity. The lysis of SG and SP by the bacteriophage ΦCJ1 was observed, showing its growth in inhibitory effects on SG and SP.

Furthermore, the stability of ΦCJ1 was examined under various temperature and pH conditions, resulting in that ΦCJ1 stably maintains in a wide range of pH environments from pH 2.5 to pH 9.0 and in a high temperature environment from 37° C. to 70° C., and even after high-temperature drying (at 60° C. for 120 minutes). These results indicate that the bacteriophage ΦCJ1 of the present invention can be readily applied to various products for the control of SG and SP.

In accordance with another aspect, the present invention relates to a composition for the prevention or treatment of Fowl Typhoid or Pullorum disease caused by *Salmonella* Gallinarum or *Salmonella* Pullorum, comprising the bacteriophage as an active ingredient.

The bacteriophage of the present invention has a specific bactericidal activity against *Salmonella* Gallinarum and *Salmonella* Pullorum, and thus can be used for the purpose of preventing or treating diseases that are caused by *Salmonella* Gallinarum and *Salmonella* Pullorum. Specifically, in the preferred embodiment, antibiotics may be included.

As used herein, the term "prevention" means all of the actions in which the disease is restrained or retarded by the administration of the composition. As used herein, the term "treatment" means all of the actions in which the disease has taken a turn for the better or been modified favorably by the administration of the composition.

Preferred examples of infectious diseases, to which the composition of the present invention can be applied, include Fowl Typhoid caused by *Salmonella* Gallinarum and Pullorum disease caused by *Salmonella* Pullorum, but are not limited thereto.

The composition of the present invention comprises ΦCJ1 of $5\times10^2$ to $5\times10^{12}$ pfu/ml, preferably $1\times10^6$ to $1\times10^{10}$ pfu/ml.

The composition of the present invention may additionally include a pharmaceutically acceptable carrier, and be formulated together with the carrier to provide foods, medicines, and feed additives.

As used herein, the term "pharmaceutically acceptable carrier" refers to a carrier or diluent that does not cause significant irritation to an organism and does not abrogate the biological activity and properties of the administered compound.

For formulation of the composition into a liquid preparation, a pharmaceutically acceptable carrier which is sterile and biocompatible may be used such as saline, sterile water, Ringer's solution, buffered physiological saline, albumin infusion solution, dextrose solution, maltodextrin solution, glycerol, and ethanol. These materials may be used alone or in any combination thereof. If necessary, other conventional additives may be added such as antioxidants, buffers, bacteriostatic agents, and the like. Further, diluents, dispersants, surfactants, binders and lubricants may be additionally added to the composition to prepare injectable formulations such as aqueous solutions, suspensions, and emulsions, or oral formulations such as pills, capsules, granules, or tablets.

Examples of the oral dosage forms suitable for the composition of the present invention include tablets, troches, lozenges, aqueous or emulsive suspensions, powder or granules, emulsions, hard or soft capsules, syrups, or elixirs. For formulation such as tablets and capsules, useful are a binder such as lactose, saccharose, sorbitol, mannitol, starch, amylopectin, cellulose or gelatin, an excipient such as dicalcium phosphate, a disintegrant such as corn starch or sweet potato starch, a lubricant such as magnesium stearate, calcium stearate, sodium stearylfumarate, or polyethylene glycol wax. For capsules, a liquid carrier such as a lipid may be further used in addition to the above-mentioned compounds.

For non-oral administration, the composition of the present invention may be formulated into injections for subcutaneous, intravenous, or intramuscular routes, suppositories, or sprays inhalable via the respiratory tract, such as aerosols. Injection preparations may be obtained by dissolving or suspending the composition of the present invention, together with a stabilizer or a buffer, in water and packaging the solution or suspension in ampules or vial units. For sprays, such as aerosol, a propellant for spraying a water-dispersed concentrate or wetting powder may be used in combination with an additive.

In accordance with still another aspect, the present invention relates to an antibiotic, comprising the composition for the prevention or treatment of Fowl Typhoid caused by *Salmonella* Gallinarum or Pullorum disease caused by *Salmonella* Pullorum.

As used herein, the term "antibiotic" means any drug that is applied to animals to kill pathogens, and used herein as a general term for antiseptics, bactericidal agents and antibacterial agents. The bacteriophage of the present invention, unlike the conventional antibiotics, has a high specificity to *Salmonella* Gallinarum and *Salmonella* Pullorum to kill the specific pathogens without affecting beneficial bacteria, and does not induce resistance so that its life cycling is comparatively long.

In accordance with still another aspect, the present invention relates to a poultry feed and drinking water for poultry, comprising the bacteriophage as an active ingredient.

The bacteriophage of the present invention may be separately prepared as a feed additive, and then added to the animal feed, or directly added to the animal feed. The bacteriophage of the present invention may be contained in the animal feed as a liquid or in a dried form. The drying process may be performed by air drying, natural drying, spray drying, and freeze-drying, but is not limited thereto. The bacteriophage of the present invention may be added as a powder form in an amount of 0.05 to 10% by weight, preferably 0.1 to 2% by weight, based on the weight of animal feed.

The feed comprising ΦCJ1 of the present invention may include plant-based feeds, such as grain, nut, food byproduct, seaweed, fiber, drug byproduct, oil, starch, meal, and grain byproduct, and animal-based feeds such as protein, mineral, fat, single cell protein, zooplankton, and food waste, but is not limited thereto.

The feed additive comprising ΦCJ1 of the present invention may include binders, emulsifiers, and preservatives for the prevention of quality deterioration, amino acids, vitamins, enzymes, probiotics, flavorings, non-protein nitrogen, silicates, buffering agents, coloring agents, extracts, and oligosaccharides for the efficiency improvement, and other feed premixtures, but is not limited thereto.

Further, the supply of drinking water mixed with the bacteriophage of the present invention can reduce the number of *Salmonella* Gallinarum or *Salmonella* Pullorum in the intestine of livestock, thereby obtaining *Salmonella* Gallinarum or *Salmonella* Pullorum-free livestock.

In accordance with still another aspect, the present invention relates to a sanitizer and a cleaner, comprising the bacteriophage as an active ingredient.

In order to remove *Salmonella* Gallinarum and *Salmonella* Pullorum, the sanitizer comprising the bacteriophage as an active ingredient can be used in the poultry barns, slaughterhouses, contaminated areas, and other production facilities, but is not limited thereto.

Further, the cleaner comprising the bacteriophage as an active ingredient can be applied to the contaminated skin, feather, and other contaminated body parts of living poultry, in order to remove *Salmonella* Gallinarum and *Salmonella* Pullorum.

In accordance with still another aspect, the present invention relates to a method for preventing or treating infectious diseases, Fowl Typhoid or Pullorum disease caused by *Salmonella* Gallinarum or *Salmonella* Pullorum using the composition for the prevention or treatment of Fowl Typhoid caused by *Salmonella* Gallinarum or Pullorum disease caused by *Salmonella* Pullorum.

The composition of the present invention may be administered into animals in a pharmaceutical formulation or as a component of the animal feed or in their drinking water, preferably administered by mixing into the animal feed as a feed additive.

The composition of the present invention may be administered in a typical manner via any route such as oral or parenteral routes, in particular, oral, rectal, topical, intravenous, intraperitoneal, intramuscular, intraarterial, transdermal, intranasal, and inhalation routes.

The method for treating the diseases of the present invention includes administration of a pharmaceutically effective amount of the composition of the present invention. It will be obvious to those skilled in the art that the total daily dose should be determined through appropriate medical judgment by a physician. The therapeutically effective amount for patients may vary depending on various factors well known in the medical art, including the kind and degree of the response to be achieved, the patient's condition such as age, body weight, state of health, sex, and diet, time and route of administration, the secretion rate of the composition, the time period of therapy, concrete compositions according to whether other agents are used therewith or not, etc.

Hereinafter, the present invention will be described in more detail with reference to the following Examples. However, these Examples are for illustrative purposes only, and the invention is not intended to be limited by these Examples.

EXAMPLES

Example 1

*Salmonella* Bacteriophage Isolation 1-1. Bacteriophage Screening and Single Bacteriophage Isolation 50 ml of a sample from the chicken slaughterhouse and sewage effluent was transferred to a centrifuge tube and centrifuged at 4000 rpm for 10 minutes. Then, the supernatant was filtered using a 0.45 μm filter. 18 ml of sample filtrate was mixed with 150 μl of SP shaking culture medium ($OD_{600}$=2) and 2 ml of 10× Luria-Bertani medium (Hereinbelow, designated as LB medium, tryptone 10 g; yeast extract 5 g; NaCl 10 g; final volume to 1 L). The mixture was cultured at 37° C. for 18 hours, and the culture medium was centrifuged at 4000 rpm for 10 minutes. The supernatant was filtered using a 0.2 μm filter. 3 ml of 0.7% agar (w/v) and 150 μl of SP shaking culture medium ($OD_{600}$=2) were mixed, and plated onto an LB plate, and changed to a solid medium. 10 μl of culture filtrate was spread thereon, and cultured for 18 hours at 37° C. (0.7% agar was used as "top-agar", and the titration of phage lysate was performed on the top-agar, called soft agar overlay method).

The sample culture medium containing the phage lysate was diluted, and mixed with 150 μl of SP shaking culture medium ($OD_{600}$=2), followed by the soft agar overlay method, so that single plaques were obtained. Since a single plaque represents one bacteriophage, to isolate single bacteriophages, one plaque was added to 400 ul of SM solution (NaCl, 5.8 g; $MgSO_4 7H_2O$, 2 g; 1 M Tris-Cl (pH7.5), 50 ml; $H_2O$, final volume to 1 L), and left for 4 hours at room temperature to isolate single bacteriophages. To purify the bacteriophage in large quantities, 100 μl of supernatant was taken from the single bacteriophage solution, and mixed with 12 ml of 0.7% agar and 500 μl of SP shaking culture medium, followed by the soft agar overlay method on an LB plate (150 mm diameter). When lysis was completed, 15 ml of SM solution was added to the plate. The plate was gently shaken for 4 hours at room temperature to elute the bacteriophages from the top-agar. The solution containing the eluted bacteriophages was recovered, and chloroform was added to a final volume of 1%, and mixed well for 10 minutes. The solution was centrifuged at 4000 rpm for 10 minutes. The obtained supernatant was filtered using a 0.2 μm filter, and stored in the refrigerator.

1-2. Large-Scale Culture of Bacteriophage

The selected bacteriophages were cultured in large quantities using SP. SP was shaking-cultured, and an aliquot of $1.5\times10^{10}$ cfu (colony forming unit) was centrifuged at 4000 rpm for 10 minutes, and the pellet was re-suspended in 4 ml of SM solution. The bacteriophage of $7.5\times10^{7}$ pfu (plaque forming unit) was inoculated thereto (MOI: multiplicity of infection=0.005), and left at 37° C. for 20 minutes. The solution was inoculated into 150 ml of LB media, and cultured at 37° C. for 5 hours. Chloroform was added to a final volume of 1%, and the culture solution was shaken for 20 minutes. DNase I and RNase A were added to a final concentration of 1 μg/ml, respectively. The solution was left at 37° C. for 30 minutes. NaCl and PEG (polyethylene glycol) were added to a final concentration of 1 M and 10% (w/v), respectively and left at 37° C. for an additional 3 hours. The solution was centrifuged at 4° C. and 12000 rpm for 20 minutes to discard the supernatant. The pellet was re-suspended in 5 ml of SM solution, and left at room temperature for 20 minutes. 4 ml of chloroform was added thereto and mixed well, followed by centrifugation at 4° C. and 4000 rpm for 20 minutes. The supernatant was filtered using a 0.2 μm filter, and ΦCJ1 was purified by glycerol density gradient ultracentrifugation (density: 40%, 5% glycerol at 35,000 rpm and 4° C. for 1 hour). The purified ΦCJ1 was re-suspended in 300 μl of SM solution, followed by titration.

Example 2

Examination on ΦCJ1 Infection of *Salmonella*

To examine the lytic activity of the selected bacteriophages on other *Salmonella* species as well as SP, cross-infection attempts with other *Salmonella* species were made. As a result, ΦCJ1 did not infect ST (*Salmonella enterica* Serotype Typhimurium), SE (*Salmonella enterica* Serotype Enteritis), SC (*Salmonella enterica* Serotype Choleraesuis), SD (*Salmonella enterica* Serotype Derby), SA (*Salmonella enterica* subsp. *Arizonae*), SB (*Salmonella enterica* subsp. *Bongori*), but specifically infected SG and SP (see Example 13). The results are shown in the following Table 1. The bacteriophages ΦCJ1 produced using SG as a host cell showed the same plaque size and plaque turbidity, and the same protein patterns and genome size as those produced using SP as a host cell.

TABLE 1

ΦCJ1 infection of *Salmonella*

| Sero Type | Strain name | Plaque formation |
|---|---|---|
| SG | SGSC 2293 | ○ |
| SP | SGSC 2294 | ○ |
| | SGSC 2295 | ○ |
| ST | ATCC 14028 | X |
| | LT2 | X |
| | UK1 | X |
| SE | SGSC 2282 | X |
| SC | ATCC 13312 | X |
| SD | SCSG 2467 | X |
| | SGSC 2468 | X |
| SA | ATCC 13314 | X |
| SB | ATCC 43975 | X |

* ATCC: The Global Bioresource Center
* SGSC: *salmonella* genetic stock center

Example 3

Morphology Examination of Bacteriophage ΦCJ1

The purified ΦCJ1 was diluted in 0.01% gelatin solution, and then fixed in 2.5% glutaraldehyde solution. After the sample was dropped onto a carbon-coated mica plate (ca.2.5×2.5 mm) and adapted for 10 minutes, it was washed with sterile distilled water. Carbon film was mounted on a copper grid, and stained with 4% uranyl acetate for 30-60 seconds, dried, and examined under a JEM-1011 transmission electron microscope (80 kV, magnification of ×120,000~×200,000). As a result, the purified ΦCJ1 had morphological characteristics including an isometric capsid and a long non-contractile tail, as shown in FIG. 1, indicating that it belongs to the morphotype group of the family Siphoviridae.

Example 4

Protein Pattern Analysis of Bacteriophage ΦCJ1

Figure 2:
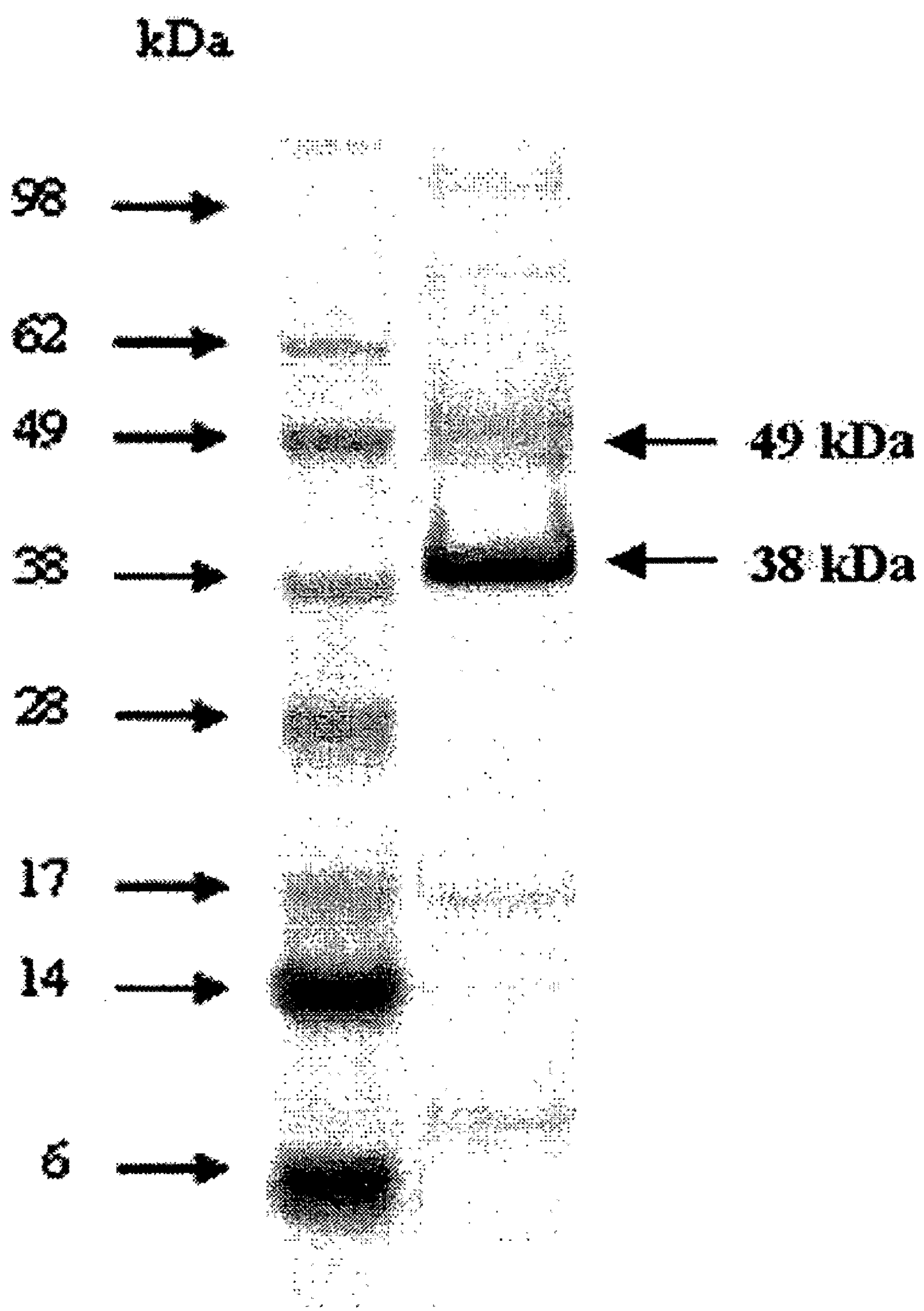

15 μl of purified ΦCJ1 solution ($10^{11}$ pfu/ml titer) was treated with 3 μl of 5×SDS sample solution, and heated for 5 minutes. The total protein of ΦCJ1 was run in 4-12% NuPAGE Bis-Tris gel (Invitrogen), and then the gel was stained with coomassie blue for 1 hour at room temperature. As shown in FIG. 2, the protein patterns showed that 38 kDa and 49 kDa bands were observed as major proteins, and 8 kDa, 17 kDa, 80 kDa, and 100 kDa bands were also observed.

Example 5

Total Genomic DNA Size Analysis of Bacteriophage ΦCJ1

Figure 3:
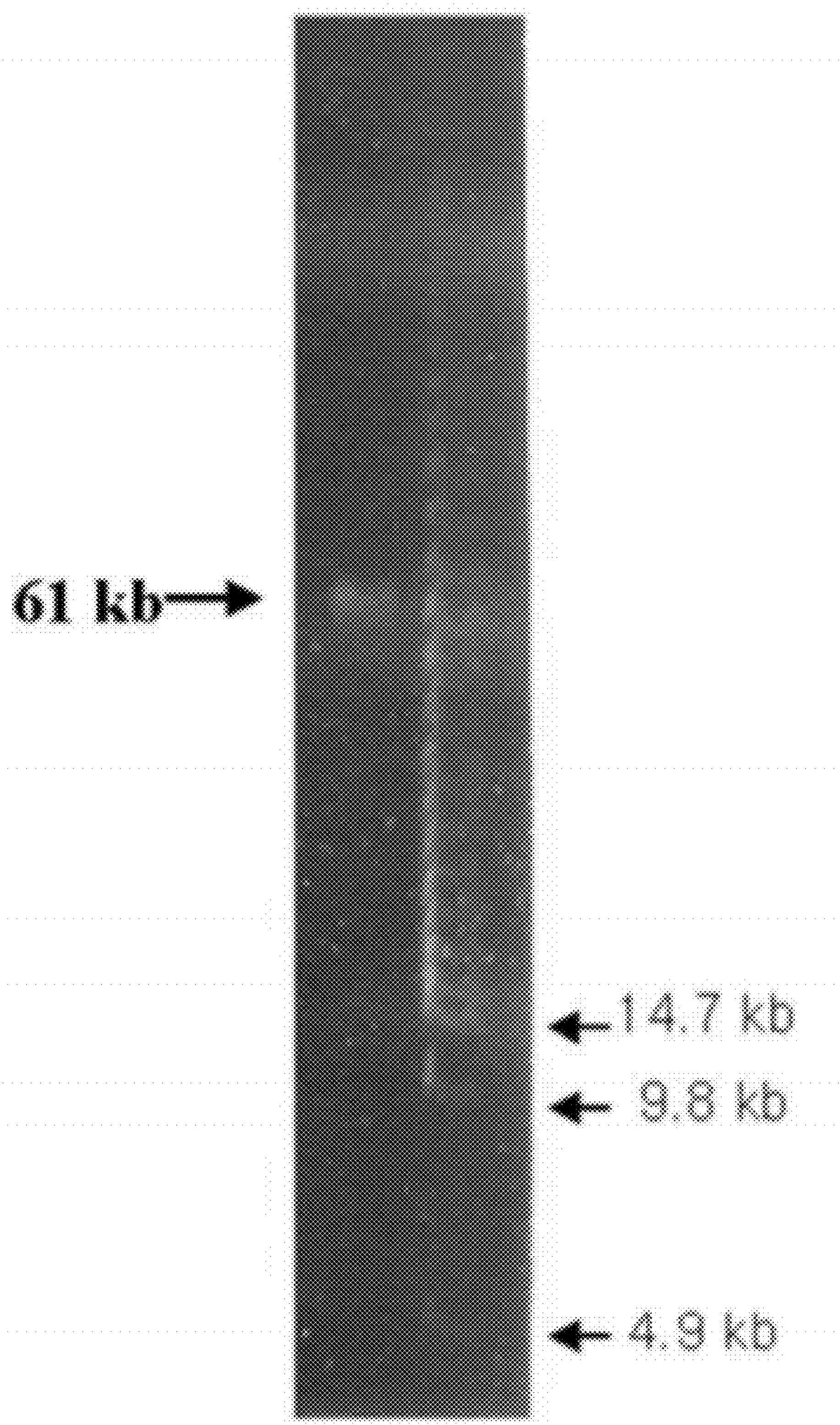

Genomic DNA was isolated from the purified ΦCJ1 by ultracentrifugation. Specifically, to the purified ΦCJ1 culture medium, EDTA (ethylenediaminetetraacetic acid (pH8.0)), proteinase K, and SDS (sodium dodecyl sulfate) were added to a final concentration of 20 mM, 50 μg/ml, and 0.5% (w/v), respectively and left at 50° C. for 1 hour. An equal amount of phenol (pH8.0) was added and mixed well, followed by centrifugation at 12000 rpm and room temperature for 10 minutes. The supernatant was mixed well with an equal amount of PC (phenol:chloroform=1:1), followed by centrifugation at 12000 rpm and room temperature for 10 minutes. The supernatant was mixed well with an equal amount of chloroform, followed by centrifugation at 12000 rpm and room temperature for 10 minutes. Again, to the supernatant, added were 1/10 volume of 3 M sodium acetate and two volumes of cold 95% ethanol, and left at −20° C. for 1 hour. After centrifugation at 0° C. and 12000 rpm for 10 minutes, the supernatant was completely removed, and the DNA pellet was dissolved in 50 μl TE (Tris-EDTA (pH 8.0)). The extracted DNA was diluted 10-fold, and its absorbance was measured at $OD_{260}$. After loading 1 μg of total genomic DNA in 1% PFGE (pulse-field gel electrophoresis) agarose gel, electrophoresis was performed using a BIORAD PFGE system program 7 (size range 25-100 kbp; switch time ramp 0.4-2.0 seconds, linear shape; forward voltage 180 V; reverse voltage 120 V) at room temperature for 20 hours. As shown in FIG. 3, ΦCJ1 had a genomic DNA size of approximately 61 kbp.

Example 6

Genetic Analysis of Bacteriophage ΦCJ1

To analyze genetic features of the purified ΦCJ1, 5 μg of genomic DNA of ΦCJ1 was treated with the restriction enzymes, EcoR V and Sca I. The vector, pBluescript SK+ (Promega) was digested with EcoR V, and treated with CIP (calf intestinal alkaline phosphatase). The digested genomic DNA and vector were mixed in a ratio of 3:1, and ligated at 16° C. for 5 hours. The ligation product was transformed into *E. coli* DH5α. The transformed cells were plated on an LB plate containing ampicillin and X-gal (5-bromo-4-chloro-3-indolyl-beta-D-galactopyranoside) for blue/white selection, so as to select two colonies. The selected colony was shaking-cultured in a culture medium containing ampicillin for 16 hours. Then, plasmids were extracted using a plasmid purification kit (Promega).

The cloning of the plasmids was confirmed by PCR using a primer set of M13 forward and M13 reverse, and insert fragments of 1 kbp or more were selected, and their base sequence was analyzed using the primer set of M13 forward and M13 reverse. The results were shown in SEQ ID NOs. 1 to 5. Sequence similarity was analyzed using a NCBI blastx program, and the results are shown in Table 2.

As shown in Table 2, ΦCJ1 showed 36% sequence similarity with Dcm of bacteriophage TLS in the forward sequence of SEQ ID NO. 1, and 31% sequence similarity with DR0530-like primase of *Burkholderia cepacia* phage BcepNazgul in the backward sequence. The backward sequence of SEQ ID NO. 1 showed 34% sequence similarity with tail spike protein of *salmonella* phage Det7. The comparison with proteins of the known bacteriophages showed low similarity, and the base sequence analysis of SEQ ID NOs. 1 to 5 by the NCBI blastn program resulted in no sequence similarity. These results indicate that ΦCJ1 is a novel bacteriophage.

TABLE 2

Sequence similarity comparison of ΦCJ1 with other bacteriophages

| | organism | protein | Accession number | Subject location | Query location | identities | E value |
|---|---|---|---|---|---|---|---|
| 1 | Bacteriophage TLS | Dcm | AAR09305 | 34-211 | 827-1351 | 66/181 (36%) | 4e−28 |
| | *Burkholderia cepacia* phage BcepNazgul | DR0530-like primase | AAQ63375 | 591-799 | 6-635 | 70/220 (31%) | 2e−18 |
| 2 | *Salmonella* phage Det7 | tailspike protein | CAO78738 | 194-700 | 1926-430 | 178/510 (34%) | 4e−76 |
| | *Salmonella* phage SETP3 | tail component protein | ABN47332 | 1-357 | 469-584 | 38/119 (31%) | 5e−09 |
| 3 | *Pseudomonas* phage D3 | Orf65 | NP_061561.1\| | 67-151 | 826-587 | 32/89 (35%) | 0.010 |
| | *Pseudomonas* phage PA11 | hypothetical protein ORF003 | YP_001294596.1 | 61-92 | 826-732 | 18/32 (56%) | 0.039 |
| 4 | *Pseudomonas* phage 73 | putative DNA polymerase | YP_001293408 | 403-519 | 4-357 | 43/118 (36%) | 6e−14 |
| | *Bacillus cereus* E33L | GIY-YIG catalytic domain - containing protein | YP_085011 | 2-109 | 440-769 | 38/110 (34%) | 2e−10 |
| 5 | Phage phiJL001 | gp77 | YP_224001.1\| | 38-130 | 627-328 | 36/100 (36%) | 3e−06 |
| | *Pseudomonas* phage 73 | hypothetical protein ORF019 | YP_001293426.1 | 53-132 | 988-770 | 32/80 (40%) | 7e−07 |

Example 7

Construction of ΦCJ1-Specific Primer Sequence

Figure 4:
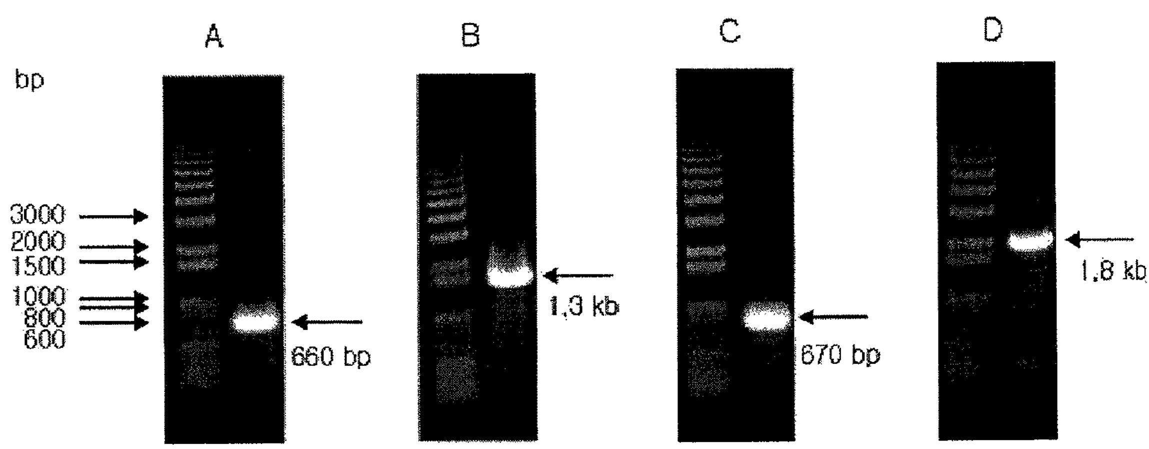

To identify ΦCJ1, ΦCJ1-specific primers were constructed. The PCR primer sets of SEQ ID NOs. 6 and 7, and SEQ ID NOs. 10 and 11 were constructed on the basis of SEQ ID NO. 1. In addition, the PCR primer sets of SEQ ID NOs. 8 and 9, and SEQ ID NOs. 12 and 13 were constructed on the basis of SEQ ID NO. 2. Further, each primer set of SEQ ID NOs. 14 and 15, SEQ ID NOs. 16 and 17, and SEQ ID NOs. 18 and 19 was constructed on the basis of SEQ ID NOs. 3, 4 and 5. PCR was performed using each primer set of SEQ ID NOs. 6 and 7, SEQ ID NOs. 10 and 11, SEQ ID NOs. 8 and 9, SEQ ID NOs. 12 and 13, SEQ ID NOs. 14 and 15, SEQ ID NOs. 16 and 17, and SEQ ID NOs. 18 and 19. 0.1 μg of genomic DNA of bacteriophage and 0.5 pmol of primer were added to a pre-mix (Bioneer), and the final volume was adjusted to 20 μl. PCR was performed with 30 cycles of denaturation; 94° C. 30 sec, annealing; 60° C. 30 sec, and polymerization; 72° C., 1 min. When SEQ ID NOs. 3 and 4, and SEQ ID NOs. 7 and 8 were used as primer sets, PCR products of approximately 660 by and 1.3 kbp were obtained, respectively. In addition, when SEQ ID NOs. 5 and 6, and SEQ ID NOs. 9 and 10 were used as primer sets, PCR products of approximately 670 by and 1.8 kbp were obtained, respectively. The results are shown in FIG. 4. In addition, when SEQ ID NOs. 14 and 15, SEQ ID NOs. 16 and 17, and SEQ ID NOs. 18 and 19 were used as primer set, PCR products of approximately 1 kbp were obtained (data not shown).

Example 8

Test on Infection Efficiency of Bacteriophage

To test the infection efficiency of the bacteriophage ΦCJ1, a one-step growth experiment was performed.

Figure 5:
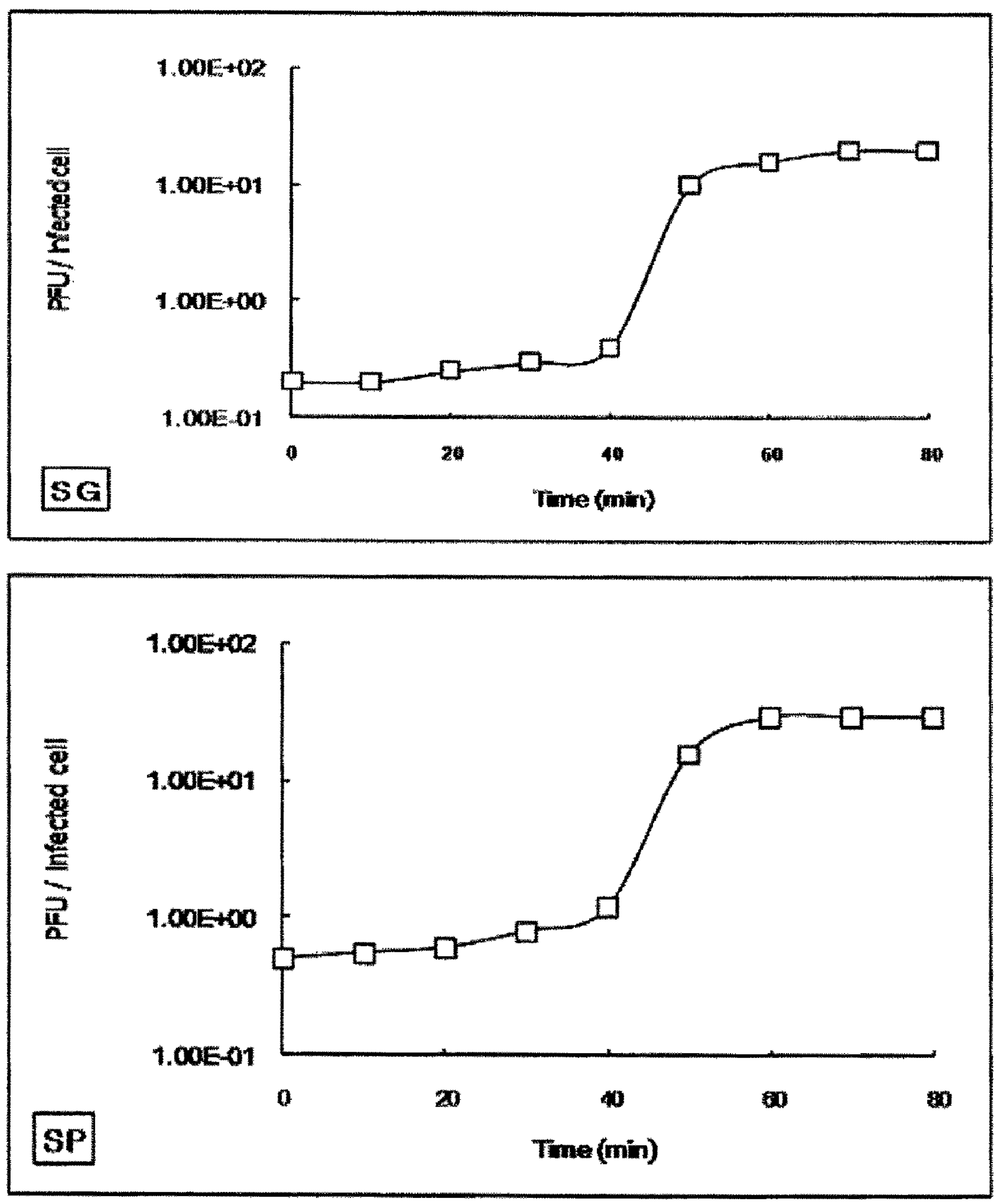
FIG. 5 is the result of a one-step growth experiment of the bacteriophage ΦCJ1, in which (A; *Salmonella* Gallinarum, B; *Salmonella* Pullorum) the bacteriophage had the burst size of $10^2$ or more in *Salmonella* Gallinarum and *Salmonella* Pullorum.

50 ml of SG culture medium ($OD_{600}$=0.5) was centrifuged at 4000 rpm for 10 minutes, and resuspended in 25 ml of fresh LB medium. The purified bacteriophage (MOI=0.0005) was inoculated thereto, and left for 5 minutes. The reaction solution was centrifuged at 4000 rpm for 10 minutes, and the cell pellet was re-suspended in fresh LB medium. While the cells were cultured at 37° C., two samples of cell culture medium were collected every 10 minutes, and centrifuged at 12000 rpm for 3 minutes. The obtained supernatant was serially diluted, and 10 μl of each diluted sample was cultured at 37° C. for 18 hours by the soft agar overlay method, and the titration of phage lysates was performed. ΦCJ1 is a bacteriophage that is able to infect SG and SP, simultaneously. Thus, the same experiment was performed on SP. The result of the one-step growth experiment on SG and SP showed the burst size of $10^2$ or more. The results are shown in FIG. 5.

Example 9

Examination of Bacteriophage Efficiency

Figure 6:
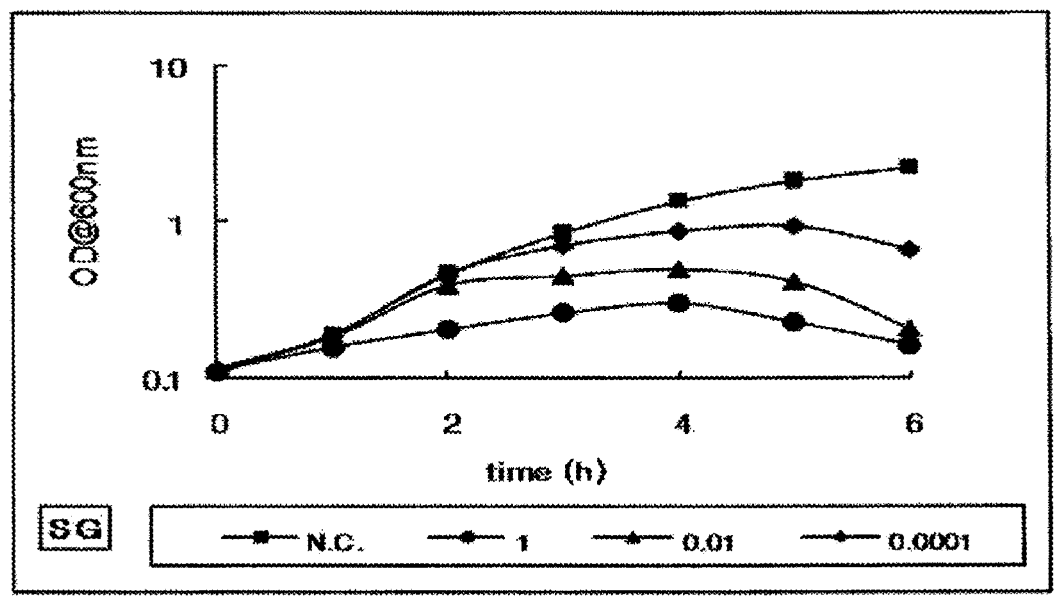
FIG. 6 is the result of an efficiency test (clearing assay) of the bacteriophage ΦCJ1, in which (A; *Salmonella* Gallinarum, B; *Salmonella* Pullorum, MOI (multiply of infection): the number of bacteriophage inoculated per host cell) as the bacteriophage ΦCJ1 has higher efficiency infection, it can effectively lyse host cells.
Figure 6:
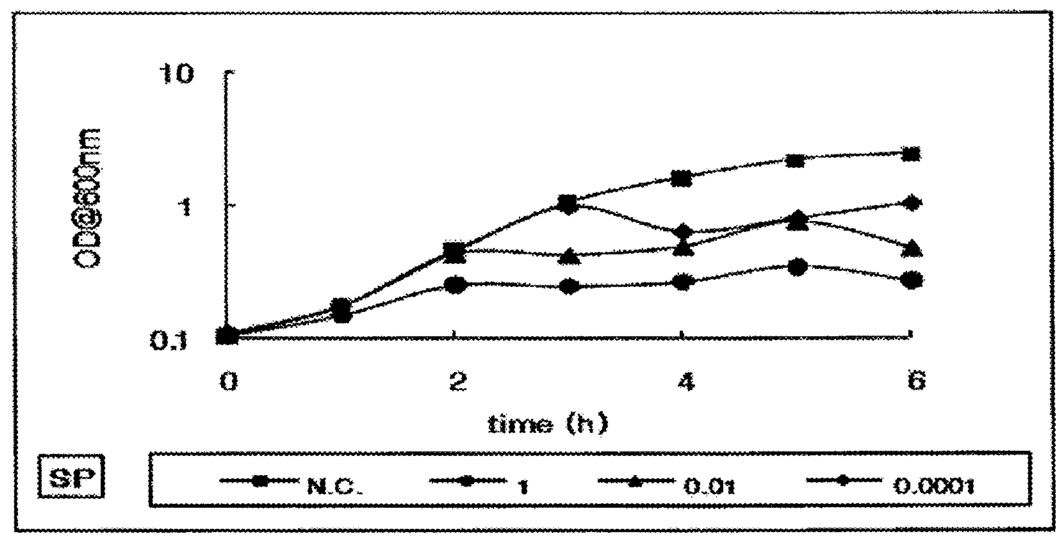

To examine the efficiency of ΦCJ1 in a liquid medium on SG, a clearing assay was performed under various conditions. 35 ml of LB medium was added to a 250 ml flask, and the bacteriophage single plaque and the SG cell were inoculated thereto in a cell ratio of 1:1, 1:100, and 1:10000, and then cultured at 37° C. and 200 rpm. The changes in $OD_{600}$ were monitored at each time interval. As a result, the inhibitory effects of ΦCJ1 on SG and SP growth were observed. The results are shown in FIG. 6.

Example 10 pH Stability Test on Bacteriophage

Figure 7:
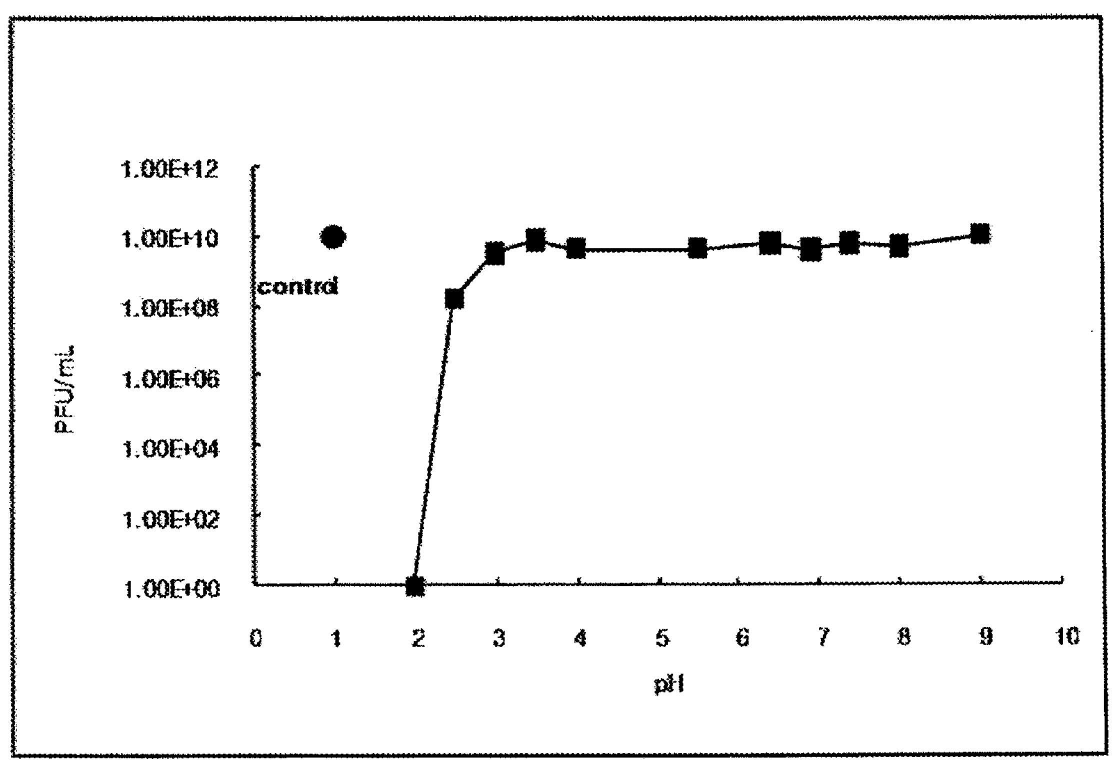
FIG. 7 is the result of an acid-resistance test on the bacteriophage ΦCJ1, showing the number of surviving bacteriophage at pH 2.1, 2.5, 3.0, 3.5, 4.0, 5.5, 6.4, 6.9, 7.4, 8.0, 9.0, in which the bacteriophage ΦCJ1 did not lose its activity until pH 2.5, but completely lost its activity at pH 2.1, as compared to the control.

To test the stability of ΦCJ1 in a low-pH environment like a chicken stomach, the stability test was performed in a wide range of pH levels (pH 2.1, 2.5, 3.0, 3.5, 4.0, 5.5, 6.4, 6.9, 7.4, 8.2, 9.0). Various pH solutions (Sodium acetate buffer (pH 2.1, pH 4.0, pH 5.5, pH 6.4)), Sodium citrate buffer (pH 2.5, pH 3.0, pH 3.5), Sodium phosphate buffer (pH 6.9, pH 7.4), Tris-HCl (pH 8.2, pH 9.0)) were prepared at a concentration of 2 M. 100 μl of a pH solution was mixed with an equal amount of bacteriophage solution ($1.0\times10^{11}$ pfu/ml) to the concentration of each pH solution to 1 M, and left at room temperature for 1 hour. The reaction solution was serially diluted, and 10 μl of each diluted sample was cultured at 37° C. for 18 hours by the soft agar overlay method, and the titration of phage lysates was performed. Changes in the titers according to pH difference were compared to examine the relative stability. The results showed that the bacteriophage did not lose its activity and maintained stability until pH 2.5. However, it lost its activity at pH 2.1. The results are shown in FIG. 7.

Example 11

Heat Stability Test on Bacteriophage

To test the stability of the bacteriophage to heat generated during the formulation process when used as a feed additive, the following experiment was performed. 200 μl of ΦCJ1 solution ($1.0\times10^{11}$ pfu/ml) was left at 37° C., 45° C., 53° C., 60° C., 70° C., and 80° C. for 0 min, 10 min, 30 min, 60 min, and 120 min, respectively. The solution was serially diluted, and 10 μl of each diluted sample was cultured at 37° C. for 18 hours by soft agar overlay method, and the titration of phage lysates was performed. Changes in the titers according to temperature and exposure time were compared to examine the relative stability. The results showed that the bacteriophage did not lose its activity at 70° C. until the exposure time of 2 hours. However, the bacteriophage rapidly lost its activity at 80° C. or higher after exposure for 10 minutes, but the activity was constantly maintained. The results are shown in FIG. 8.

Example 12

Dry Stability Test on Bacteriophage

To test the stability of the bacteriophage under the dry conditions during the formulation process when used as a feed additive, the following experiment was performed. On the basis of the results of the heat stability test, the experiment was performed under high-temperature drying conditions (at 60° C. for 120 min). 200 μl of ΦCJ1 solution ($1.0\times10^{11}$ pfu/ml) was dried using a Speed vacuum (Speed-Vacuum Concentrator 5301, Eppendorf). The obtained pellet was completely re-suspended in an equal amount of SM solution at 4° C. for one day. The solution was serially diluted, and 10 μl of each diluted sample was cultured at 37° C. for 18 hours by the soft agar overlay method, and the titration of phage lysates was performed. Changes in the titers before and after drying were compared to examine the relative stability. The results showed that its activity was decreased to $10^2$. The results are shown in FIG. 9.

Example 13

Examination of Bacteriophage Infection of Wild-Type SG/SP

The lytic activity of bacteriophage ΦCJ1 was tested for 15 and 5 strains of the Korean wild-type SG and SP, isolated by Laboratory of Avian Diseases, College of Veterinary Medicine, Seoul National University, in addition to SG (SG RKS4994) and SP(SP RKS2242) used in the present invention. 150 μl of each strain shaking culture medium ($OD_{600}$=2) was mixed, and 10 μl of ΦCJ1 solution ($10^{10}$ pfu/ml) was cultured at 37° C. for 18 hours by the soft agar overlay method, and the plaque formation was examined. It was found that the bacteriophage ΦCJ1 showed 100% lytic activity on the wild-type SG and SP. The results are shown in Table 3.

TABLE 3

Lytic activity on Korean wild-type SG and SP

| Sero type | Strain name | ΦCJ1 plaque formation |
|---|---|---|
| SG | SNU SG1 | ○ |
| | SNU SG2 | ○ |
| | SNU SG3 | ○ |
| | SNU SG4 | ○ |
| | SNU SG5 | ○ |
| | SNU SG6 | ○ |
| | SNU SG7 | ○ |
| | SNU SG8 | ○ |
| | SNU SG9 | ○ |
| | SNU SG10 | ○ |
| | SNU SG11 | ○ |
| | SNU SG12 | ○ |
| | SNU SG13 | ○ |
| | SNU SG14 | ○ |
| | SNU SG15 | ○ |
| SP | SNU SP1 | ○ |
| | SNU SP 4 | ○ |
| | SNU SP 5 | ○ |
| | SNU SP 8 | ○ |
| | SNU SP 11 | ○ |

* SG/SP source: Laboratory of Avian Diseases, College of Veterinary Medicine, Seoul National University Example 14

Toxicity Test on Bacteriophage

A toxicity test on the bacteriophage ΦCJ1 for the prevention of Fowl Typhoid was performed by evaluation of its safety, residual amount, and eggs in layer chickens. The layer chickens are divided into three groups to perform a pathogenicity test and egg test, and to examine the presence of clinical signs and phage content in the cecal feces.

For the pathogenicity test, 13 brown layer chickens were divided into a ΦCJ1-treated group with 8 layers and a control group with 5 layers. The ΦCJ1-treated group was fed with a mixture of feed and ΦCJ1 ($10^8$ pfu or more per feed (g)) and the control group was fed with feed only, and egg production rate and clinical signs were examined for 3 weeks after phage treatment. As shown in Table 4, the ΦCJ1-treated group and the control group showed about 42% and 50% egg production rates, respectively. In addition, clinical signs after phage treatment were examined, resulting in that respiratory and digestive lesions were not observed for 24 days after ΦCJ1 treatment, and abnormal activity was not observed. The results indicate that ΦCJ1 treatment does not generate adverse effects.

For the egg test, 10 eggs were collected on day 3, 6, and 9 after ΦCJ1 treatment, and the egg surface was washed with 70% ethanol and broken out. Egg yolk and egg white were mixed, and 5 ml of the mixture was diluted with 45 ml of PBS by $10^{-1}$, $10^{-2}$, and $10^{-3}$. $10^6$ cfu of SNUSG0197 was added to 25 ml of each diluted solution, and incubated at 37° C. for 3 hours, and cells were isolated by centrifugation. 500 μl of supernatant and 100 μl of SNUSG0197 ($10^9$ cfu/ml) were mixed with each other, and plated on a tryptic soy agar plate by the top-agar overlay technique. After incubation at 37° C. for 18 hrs, the number of plaque was counted to calculate the number of phage per 1 ml of egg. As shown in Table 5, no ΦCJ1 was found in 17 eggs that were collected on day 3, 6, and 9.

Next, the presence of clinical signs and ΦCJ1 content in the cecal feces were examined after ΦCJ1 treatment. At 3 weeks after ΦCJ1 treatment, the test layer chickens were euthanized, and necropsy was performed to examine gross lesions in the liver, spleen, kidney and ovary. The liver sample was aseptically collected with sterile cotton swab, and plated on a Mac Conkey agar plate to examine the presence of *Salmonella* Gallinarum. The cecal feces were also collected to measure the ΦCJ1 content in the individual chickens. Briefly, 1 g of cecal feces was suspended in 9 ml of PBS, and centrifuged at 15000 g for 30 min. 1 ml of supernatant was diluted with PBS by $10^{-1}$ to $10^{-4}$, and 500 μl of the dilution and 100 μl of SG0197 ($10^9$ cfu/ml) were mixed with each other, and plated on a 10× tryptic soy agar plate by the top-agar overlay technique. After incubation at 37° C. for 18 hrs, the number of plaque was counted to calculate the number of phage per cecal feces (g), taking into account the serial dilution. As a result, no abnormal clinical signs were observed during the examination period, and about $3.7\times10^4$ pfu of ΦCJ1 per cecal feces (g) was measured, indicating survival of the bacteriophage in the intestine after passing through the stomach.

Bacteriophage distribution in the organs was examined. Briefly, 10 SPF chicks (11 day-old) were divided into two groups with 5 chicks each. For 3 days, the treated group was fed with feed supplemented with $10^8$ pfu of ΦCJ1 (per g), and the control group was fed with feed only. The chicks were sacrificed to collect the liver, kidney and cecal feces, and the presence of ΦCJ1 was examined. Each of the collected liver, kidney and cecal feces was emulsified with an equal volume of PBS. 1 ml of the liver and the whole quantity of the kidney and cecal feces were transferred into 1.5 ml tubes, followed by centrifugation at 15,000 rpm for 15 min. 1 ml of supernatant was diluted with PBS by $10^{-1}$ to $10^{-4}$, and 500 μl of the dilution and 100 μl of SG0197 ($10^9$ cfu/ml) were mixed with each other, and plated on a 10× tryptic soy agar plate by the top-agar overlay technique. After incubation at 37° C. for 18 hrs, the number of plaque was counted to calculate the number of bacteriophage per cecal feces (g), taking into account the serial dilution. As shown in Table 6, ΦCJ1 was not observed in the liver and kidney, but in the cecal feces.

TABLE 4

Average egg production rate on ΦCJ1 treatment

| | ΦCJ1 | control |
|---|---|---|
| 1 day | Feeding day | |
| 2 day | | |
| 3 day | 7 | 5 |
| 6 day | 8 | 7 |
| 7 day | 3 | 3 |
| 8 day | 6 | 4 |
| 9 day | 2 | 1 |

TABLE 4-continued

| Average egg production rate on ΦCJ1 treatment | | |
|---|---|---|
| | ΦCJ1 | control |
| 10 day | 3 | 3 |
| 13 day | 11 | 8 |
| 14 day | | |
| 15 day | 10 | 7 |
| 16 day | | |
| 17 day | 6 | 6 |
| 20 day | 11 | 7 |
| 21 day | | |
| 22 day | 9 | 4 |
| 23 day | | |
| 24 day | 6 | 3 |
| Egg production rate | 42.2% | 50.8% |

TABLE 5

| Isolation frequency of ΦCJ1 | | |
|---|---|---|
| Collection day | ΦCJ1 | control |
| 3 day | 0/7 | 0/5 |
| 6 day | 0/8 | 0/7 |
| 9 day | 0/2 | 0/1 |
| Total | 0/17 | 0/13 |

TABLE 6

| Presence of phages in organs of ΦCJ1-treated group | | | | | | |
|---|---|---|---|---|---|---|
| | ΦCJ1-treated group | | | Control group | | |
| Test chicken | liver | kidney | cecal feces | liver | kidney | cecal feces |
| 1 | − | − | + | − | − | − |
| 2 | − | − | + | − | − | − |
| 3 | − | − | + | − | − | − |
| 4 | − | − | + | − | − | − |
| 5 | − | − | + | − | − | − |

Example 15

Efficacy Test on Bacteriophage

In order to evaluate the efficacy of ΦCJ1 on the prevention and treatment of SG, an efficacy test was performed in chickens.

20 brown layers (1-day-old) were divided into 10 test groups with 10 layers each ΦCJ 1 treated group+non-treated challenged group 1). For 1 week, the test chicks were fed with feed supplemented with $10^7$ pfu of ΦCJ1 (per g) and drinking water supplemented with $10^7$ pfu of ΦCJ1 (per ml). At 1 week, $10^6$ cfu of SG0197 (per chick) and $10^7$ pfu (MOI=10) of phage was mixed with 500 μl of TSB, and left in ice for 1 hour or less, followed by oral administration. The mortality rate was examined for 2 weeks. The surviving chicks were subjected to necropsy and examined for gross lesions, and the bacteria were isolated. As shown in Table 7, it was found that the ΦCJ1-treated group showed a significantly higher protection rate ($P<0.05$) than the non-treated group.

TABLE 7

| Efficacy test of ΦCJ1 in chickens | | |
|---|---|---|
| | ΦCJ1-treated challenged group | Non-treated challenged group |
| Survival | 8 | 3 |
| Mortality rate | 20% | 70% |
| Clinical signs | 1/8 | 1/3 |
| SG reisolation | 0/8 | 0/3 |
| Protection rate | 70% | 20% |

Industrial Applicability

The bacteriophage of the present invention has a specific bactericidal activity against *Salmonella* Gallinarum and *Salmonella* Pullorum without affecting beneficial bacteria, and excellent acid-, heat- and dry-resistance, and thus can be used for the prevention and treatment of Fowl Typhoid and Pullorum disease that are caused by *Salmonella* Gallinarum and *Salmonella* Pullorum, and also applied to control *Salmonella* Gallinarum and *Salmonella* Pullorum. For example, the bacteriophage is used for a composition for the prevention or treatment of infectious diseases caused by *Salmonella* Gallinarum or *Salmonella* Pullorum, feed and drinking water for poultry, sanitizers and cleaners, as an active ingredient.

All documents, articles, publications, patents, and patent applications mentioned in this specification are herein incorporated by reference to the same extent as if each individual publication or patent application was specifically and individually indicated to be incorporated by reference.

What is claimed is:

1. An isolated bacteriophage having a specific bactericidal activity against *Salmonella* Gallinarum and *Salmonella* Pullorum, which is deposited under accession number KCCM10969P.

2. A composition for the prevention or treatment of infectious diseases caused by *Salmonella* Gallinarum or *Salmonella* Pullorum, comprising the bacteriophage of claim 1 as an active ingredient.

3. The composition according to claim 2, wherein the infectious disease is selected from Fowl Typhoid and Pullorum disease.

4. An antibiotic composition comprising the bacteriophage of claim 1 as an active ingredient.

5. An animal feed or drinking water, comprising the bacteriophage of claim 1 as an active ingredient.

6. A sanitizer or cleaner, comprising the bacteriophage of claim 1 as an active ingredient.

7. A method for treating an infectious disease caused by *Salmonella* Gallinarum or *Salmonella* Pullorum, comprising administering the bacteriophage of claim 1 to an animal in need thereof.

8. A method for treating an infectious disease caused by *Salmonella* Gallinarum or *Salmonella* Pullorum, comprising administering the composition of claim 2 to an animal in need thereof.

* * * * *